United States Patent [19]

Schmidt et al.

[11] 4,294,766

[45] Oct. 13, 1981

[54] PREPARATION OF PURE POTASSIUM RIBONATE AND RIBONOLACTONE

[75] Inventors: Wolfram Schmidt, Friedelsheim; Joachim Paust, Neuhofen, both of Fed. Rep. of Germany

[73] Assignee: BASF Aktiengesellschaft, Ludwigshafen, Fed. Rep. of Germany

[21] Appl. No.: 100,724

[22] Filed: Dec. 6, 1979

[30] Foreign Application Priority Data

Dec. 6, 1978 [DE] Fed. Rep. of Germany ....... 2852721

[51] Int. Cl.$^3$ .................. C07D 307/32; C07C 59/105
[52] U.S. Cl. .................................. 260/343.6; 562/587
[58] Field of Search ....................... 562/515, 580, 587; 260/343.6

[56] References Cited

U.S. PATENT DOCUMENTS

| 2,430,855 | 11/1947 | Barch | 562/580 |
| 2,438,881 | 3/1948 | Sternbach | 260/343.6 |
| 2,438,882 | 3/1948 | Sternbach | 260/343.6 |
| 2,438,883 | 3/1948 | Flexser | 260/343.6 |
| 4,035,419 | 7/1977 | Sumikawa et al. | 562/580 |

FOREIGN PATENT DOCUMENTS 4525 6/1955 Japan .

Primary Examiner—Norma S. Milestone
Attorney, Agent, or Firm—Oblon, Fisher, Spivak, McClelland & Maier

[57] ABSTRACT

An improved process for the preparation of potassium ribonate and of ribonolactone, which is an interesting intermediate for the preparation of riboflavin (vitamin $B_2$), starting from potassium arabonate. An aqueous potassium arabonate solution is epimerized by adding a water-soluble non-ionic organic solvent, after which the greater part of the non-epimerized potassium arabonate can be separated off in a crystalline form. The mother liquor, which essentially contains potassium ribonate in addition to a small amount of unconverted potassium arabonate, is greatly concentrated and cooled, whereupon pure potassium ribonate crystallizes out; the latter can be lactonized in the conventional manner. Alternatively, the mixture of potassium arabonate and potassium ribonate, contained in the concentrated mother liquor, can be lactonized and the resulting lactone mixture, containing at least 70% by weight of ribonolactone, can be separated by fractional crystallization using dioxane or ethylene glycol monomethyl ether.

5 Claims, No Drawings

PREPARATION OF PURE POTASSIUM RIBONATE AND RIBONOLACTONE

The present invention relates to a process for the preparation of pure potassium ribonate and ribonolactone, starting from potassium arabonate.

Ribonolactone is known as an important intermediate for the preparation of riboflavin (vitamin $B_2$). Ribonolactone is obtained by lactonizing ribonic acid or its salts, ie. the ribonates. Ribonates are obtained by oxidizing glucose in aqueous sodium hydroxide solution or potassium hydroxide solution with oxygen to give a mixture of Na arabonate and Na formate, or K arabonate and K formate, respectively, from which solution the arabonate is isolated by adding a water-miscible solvent; the arabonate is subsequently epimerized by heating at 130°–140° C. in aqueous solution.

Since this epimerization always only goes to an equilibrium of about 70% of arabonate with 30% of ribonate, fractional crystallization of arabonate and ribonate is necessary. According to the prior art, the sodium salts and potassium salts are however unsuitable for such fractional crystallization, since they are very water-soluble and hardly differ in solubility. Hence, the procedure generally followed is to add calcium chloride to the aqueous solutions containing sodium arabonate and ribonate or potassium arabonate and ribonate, after which, on cooling, calcium arabonate crystallizes out preferentially (cf. Japanese Published Patent No. 4525/1955). A variant of this method is first to convert the Na arabonate or K arabonate into Ca arabonate, isolate the latter and then carry out the epimerization (cf. U.S. Pat. No. 2,438,882).

Disadvantages of the conventional processes described above are that
1. the sodium or potassium salts must first be converted to the calcium salts in order to separate the arabonates and ribonates,
2. the crystallization of the calcium salts takes a great deal of time (several days) and
3. on fractional crystallization of the said epimeric calcium salts, the ribonate obtainable is only about 80% pure.

To achieve greater purity, the Ca salts are converted to other salts, which can be purified by further crystallization. Separation methods employing the zinc, cadmium and mercury salts have been disclosed, but these are unsuitable for an industrial process because of the toxicity of the metal salts and the resulting problem of disposing of the effluent.

It is true that the iron salts, also used for this purpose, are non-toxic, but they have other important disadvantages. For example, conversion of the calcium salts to the iron salts requires heating for from 3 to 5 hours at 80°–100° C., which is industrially unattractive. Furthermore, conversion of the iron ribonate into ribonolactone gives yields of only about 80–85%, which is unsatisfactory for an industrial method of synthesis.

It is an object of the present invention to provide a possibility of preparing pure ribonolactone, required for the preparation of vitamin $B_2$, in an industrially advantageous manner which avoids the disadvantages of the conventional methods. For this, the arabonate and ribonate in the mixture arising from the epimerization of arabonate must be separated by a less expensive method and a more advantageous process for highly purifying the ribonate or ribonolactone must be developed.

We have found, surprisingly, that the above object is achieved and that the proportion of potassium ribonate in an aqueous solution containing potassium arabonate and potassium ribonate can, contrary to all expectations, be greatly increased by a very simple method if the aqueous solution is mixed with from 40 to 900% by weight, based on the amount of water, of a water-soluble, non-ionic or virtually non-ionic organic solvent and the potassium arabonate which subsequently crystallizes out is separated from the solution which essentially contains the potassium ribonate.

This crystallization process only requires from about 1 to 6 hours, but nevertheless gives a ribonate of comparable purity to that obtained by conventional methods via the calcium salts. The possibility of such an advantageous method of separation is surprising because the solubilities of K arabonate and K ribonate in the aqueous-organic solutions only differ by a factor of 2 (it may be noted, by way of comparison, that the solubility of the Ca salts in water differs by a factor of 80).

We have further found, surprisingly, that it is possible to obtain very pure potassium ribonate (of 95–98% purity) from a mixture of potassium ribonate and potassium arabonate, which contains 70% by weight or more of potassium ribonate, by fractional crystallization from water at low temperatures.

We have further found, surprisingly, that it is possible to obtain very pure ribonolactone (of 95–98% purity) from a mixture of ribonolactone and arabonolactone, which contains 70% by weight or more of ribonolactone, by fractional crystallization from suitable solvents, especially dioxane and ethylene glycol monomethyl ether.

Accordingly, the invention relates to a process for the preparation of pure potassium ribonate and ribonolactone, wherein (a) to prepare pure potassium ribonate, an aqueous potassium arabonate solution is epimerized in the conventional manner by heating at 130°–140° C., the resulting solution, containing potassium ribonate and unconverted potassium arabonate, is mixed with from 40 to 900% by weight, based on the amount of water, of a water-soluble, non-ionic or virtually non-ionic, organic solvent, the potassium arabonate which hereupon crystallizes out is then separated off, the solvent, with or without part of the water, is distilled from the remaining solution which essentially contains potassium ribonate in addition to a small amount of unconverted potassium arabonate, and the potassium ribonate is allowed to crystallize out from the purely aqueous solution at a low temprature and (b) to prepare pure ribonolactone, either the pure potassium ribonate obtained according to (a) is lactonized in the conventional manner, or the mixture contained in the solution which remains after separating off the crystallized-out potassium arabonate according to (a), which mixture essentially contains potassium ribonate in addition to a small amount of unconverted potassium arabonate, is lactonized in the conventional manner and the ribonolactone is isolated from the lactone mixture by crystallization.

To carry out the process according to the invention, an aqueous potassium arabonate solution is epimerized in the conventional manner by heating at 130°–140° C.

The solutions thereby obtained in general contain from 5 to 50, preferably from 10 to 30, % by weight of the potassium salts of the two epimeric aldonic acids, the proportion of arabonate being from about 60 to 80% and the proportion of ribonate from about 40 to 20%.

Suitable water-soluble non-ionic organic solvents for the purposes of the invention are, in particular, $C_1$–$C_4$-alkanols, eg. methanol, ethanol, isopropanol and n-butanol, cycloaliphatic ethers, eg. dioxane, and alkanediols of 2 or 3 carbon atoms which are partially etherified with methanol or ethanol. Methanol, and the monomethyl and monoethyl ether of ethylene glycol, are particularly suitable. Mixtures of water-soluble non-ionic organic solvents may also be used.

If relatively concentrated potassium arabonate/ribonate solutions, ie. solutions containing from 20 to 40% by weight of these salts, are used as starting materials, the solvents are advantageously used in amounts of from 60 to 250% by weight, based on the amount of water. This method results in relatively rapid crystallization, which requires from about 1 to 2 hours. A crystalline product comprising from 90 to 98% of arabonate and from 10 to 2% of ribonate is obtained, together with a liquid phase in which the solids comprise from 30 to 20% of arabonate and from 70 to 80% of ribonate. A somewhat better separation into a crystal phase predominantly containing arabonate and a liquid phase predominantly containing ribonate is achieved by starting from more dilute solutions of the epimeric salts, ie. from solutions containing from 5 to 15% by weight of these salts. In that case, the solvents are advantageously employed in an amount of from 200 to 400% by weight, based on water. If more dilute aqueous arabonate/ribonate solutions are used, the crystallization is advantageously carried out at from 0° to 40° C. On the other hand, where the concentrated solutions are used, temperatures of from 40° to 70° C. may be employed. This is technologically particularly advantageous because of the low volumes involved and the possibility of cooling by virtue of the environment being at ambient temperature.

Within the stated ranges of the K arabonate/ribonate concentrations, the temperature and the nature and amount of the solvent, the economically most advantageous crystallization conditions for the particular requirements involved can easily be established from a few preliminary experiments; in all cases it is advisable to initiate the crystallization of the K arabonate with a few seeding crystals.

The liquid phase, predominantly containing potassium ribonate, which is obtained after separating off the potassium arabonate, is used, after removing the added solvent by distillation, in order to prepare pure potassium ribonate or ribonolactone.

To prepare potassium ribonate, the purely aqueous solution is concentrated to from about 40 to 60% strength by weight, cooled to from about −2° to +10° C., preferably from about 0° to 5° C., and seeded with a few potassium ribonate crystals. Surprisingly, the potassium ribonate hereupon crystallizes out in very good yields and in 95–98% purity. Because of its high purity, the product thus obtained is very suitable for the synthesis of riboflavin, without requiring additional purification.

To prepare pure ribonolactone, the pure potassium ribonate can be lactonized in the conventional manner, or the purely aqueous solution predominantly containing potassium ribonate, which is obtained after removing the potassium arabonate and added solvent, can be used. The potassium salts present in this purely aqueous solution, namely potassium ribonate and a small amount of potassium arabonate, can be converted to the lactones by conventional methods, for example by treating with ion exchangers or by concentrating in the presence of sulfuric acid and then filtering off the potassium sulfate which has precipitated. This gives a crude product which consists of from 70 to 80% of ribonolactone and from 20 to 30% of arabonolactone. The possibility of purifying such a product by crystallization has not hitherto been disclosed. The reason is probably that the two lactones show only very slight solubility differences in the conventional organic solvents.

We have found that there are certain solvents from which 95–98% pure ribonolactone can be obtained by crystallization from the above crude product. Crystallization from dioxane or from ethylene glycol monomethyl ether is particularly effective.

Even in these solvents, the solubility differences between ribonolactone and arabonolactone are very slight: 10 g of arabonolactone dissolve in 75 ml of dioxane at 25° C. and 10 g of ribonolactone dissolve in 85 ml of dioxane at 25° C.; 10 g of arabonolactone dissolve in 22 ml of ethylene glycol monomethyl ether at 25° C. and 10 g of ribonolactone dissolve in 24 ml of ethylene glycol monomethyl ether at 25° C.

Hence, it is surprising that selective crystallization of ribonolactone is nevertheless possible when the crude product still contains from about 20 to 30% of arabonolactone. Crystallization from dioxane can be carried out with a solution of from 30 to 60% strength, preferably from 40 to 50% strength. The crystallization temperature is from 0° to 50° C., preferably from 5° to 30° C. Crystallization from methylglycol is carried out with a solution of from 30 to 60% strength, preferably of 50% strength, at from 0° to 40° C., preferably from 0° to 25° C. In general, it is advisable to seed the crystallizing solution with a few crystals of ribonolactone. In this way, very pure ribonolactone may be obtained.

The mixture of lactones (about 50% of arabonolactone and 50% of ribonolactone) contained in the mother liquor obtained can easily be reconverted to a mixture of the potassium salts by treatment with KOH, and be recycled to the separation process according to the invention.

Using the process according to the invention it proves possible to prepare the ribonolactone, required for the preparation of vitamin $B_2$, in an industrially very advantageous manner.

EXAMPLE 1

350 ml of ethylene glycol monomethyl ether were added to 250 g of an aqueous solution, containing 28% of potassium arabonate and 12% of potassium ribonate, at 90° C., and after adding a few seeding crystals of K arabonate, the mixture was kept for two hours at 60° C. Hereupon, 71 g (corresponding to 71% of the K arabonate employed for the epimerization) crystallized out. The remaining K arabonate was left in the solution together with 25 g of K ribonate; this means that the K ribonate obtained was about 85% pure.

The concentration of K arabonate and K ribonate was determined chromatographically on an ion exchanger.

The solution employed was obtained by epimerizing 100 g of K arabonate in 500 g of water at 140° C. The solution was decolorized with active charcoal and concentrated, before crystallization, to 250 g = 200 ml (corresponding to the weight ratios mentioned above).

EXAMPLE 2

460 g (=420 ml) of an aqueous solution which contained 15% of K arabonate and 6.5% of K ribonate were mixed with 840 ml of ethylene glycol monomethyl ether and a few crystals of K arabonate. In the course of one hour at 25° C., 69 g of K arabonate (corresponding to 69% of the K arabonate employed for the epimerization) crystallized out. 2 g of K arabonate and 29 g of K ribonate remained in the solution, which means that the K ribonate obtained was about 95% pure. As in Example 1, the concentration of the epimeric compound was determined chromatographically.

The solution employed originated from an epimerization of 100 g of K arabonate, carried out as described in Example 1, except that the resulting solution was only concentrated to 360 ml, instead of to 200 ml.

EXAMPLE 3

630 ml of methanol and a few crystals of K arabonate were added to 370 g (=330 ml) of an aqueous solution which contained 19% of K arabonate and 8% of K ribonate. In the course of 1 hour at 40° C., 63 g of K arabonate crystallized out and 29 g of K ribonate together with 6 g of K arabonate remained in the liquid phase.

The concentration of the epimeric compounds was determined chromatographically, as in Example 1. The solution employed originated from an epimerization of 100 g of K arabonate, carried out as described in Example 1, except that the resulting solution was only concentrated to 330 ml, instead of to 200 ml.

EXAMPLE 4

100 g of potassium arabonate were dissolved in 320 ml of water and epimerized by heating at 140° C. The resulting solution was decolorized with active charcoal and 480 ml of dioxane were then added whilst hot. The mixture was then cooled to room temperature. 65 g of potassium arabonate crystallized out and 24 g of potassium ribonate, together with 8 g of potassium arabonate, remained in the mother liquor.

EXAMPLE 5

A solution containing about 20 g of potassium arabonate and 80 g of potassium ribonate, as obtained by epimerizing 350 g of potassium arabonate and subsequently precipitating the greater part of the unconverted potassium arabonate by adding ethylene glycol monomethyl ether, and separating off the precipitate, was freed from solvent by distillation and concentrated to about 200 ml. The resulting aqueous solution of about 50% strength was cooled with ice water and a few crystals of potassium ribonate were added. In the course of 2 hours, about 60 g of potassium ribonate of 95–98% purity crystallized out. The yield of pure potassium ribonate was about 75% of the potassium ribonate contained in the mother liquor.

EXAMPLE 6

100 g of a crude product consisting of about 80% of ribonolactone and 20% of arabonolactone, as obtained by epimerizing potassium arabonate, precipitating and separating off the greater part of the unconverted potassium arabonate and lactonizing the epimeric potassium salts remaining in the mother liquor, were dissolved in 150 ml of dioxane, and the solution was cooled to about 10° C. and seeded with a few crystals of ribonolactone. 49 g of 98% pure ribonolactone crystallized out from the solution. The yield was 61%, based on the ribonolactone present in the crude product.

EXAMPLE 7

100 g of a crude product consisting of 70% of ribonolactone and 30% of arabonolactone were dissolved in 100 ml of hot ethylene glycol monomethyl ether and the solution was cooled to about 0° C. and seeded with a few crystals of ribonolactone. About 45 g of 95% pure ribonolactone crystallized from the solution at about 0° C. The yield was 64%.

EXAMPLE 8

100 g of potassium arabonate were dissolved in 300 ml of water and epimerized in the conventional manner by heating for 4 hours at 130°–140° C. The resulting solution was decolorized with active charcoal and 650 ml of methanol were added whilst the solution was hot. 67 g of unconverted potassium arabonate crystallized out at about 40° C.; this material could be recycled to the epimerization.

The methanol was distilled from the mother liquor. The resulting purely aqueous solution was run, in the conventional manner, over a cation exchanger in the $H^+$ form. The water was then distilled off. 21 g of a crude ribonolactone, which still contained about 20% of arabonolactone, were obtained. The resulting crude product was seeded at about 35° C. with a few crystals of ribonolactone and cooled to 5°–10° C. 10.4 g of pure ribonolactone were obtained.

EXAMPLE 9

100 g of potassium arabonate were dissolved in 300 ml of water and epimerized in the conventional manner by heating for 4 hours at 130°–140° C. The resulting solution was decolorized with active charcoal and 650 ml of methanol were added to the hot solution. At about 40° C., 67 g of unconverted potassium arabonate crystallized out; this material could be recycled to the epimerization. The methanol was distilled from the mother liquor obtained, and the resulting aqueous solution was concentrated to 60 g. During cooling, the solution was seeded with a few crystals of potassium ribonate. In the course of about 2 hours at 5° C., 17.4 g of pure potassium ribonate crystallized out.

We claim:

1. A process for the preparation of pure ribonolactone from a mixture of ribonolactone and arabonolactone, which contains 70% by weight or more of the ribonolactone, wherein the mixture is subjected to fractional crystallization from a concentrated solution in dioxane or ethylene glycol monomethyl ether at a low temperature.

2. A process for the preparation of pure potassium ribonate, comprising:
(a) epimerizing potassium arabonate in an aqueous solution at 130°–140° C. thereby forming a mixture of potassium ribonate and potassium arabonate in solution;
(b) mixing the product solution from step (a) with from 40 to 900% by wt., based on the amount of water present, of an organic solvent selected from the group consisting of $C_1$–$C_4$ alkanols, cycloaliphatic ethers, alkanediols of 2 or 3 carbon atoms which are partially etherified with methanol or ethanol and mixtures thereof and allowing most of the potassium arabonate present to crystallize from solution;

(c) removing the solvent from said aqueous potassium ribonate containing solution;

(d) concentrating the aqueous solution to a salt strength from about 40 to 60% by weight;

(e) crystallizing the potassium ribonate from the solvent free, concentrated aqueous solution at from about −2° to 10° C.

3. The method of claim 2, wherein, when the aqueous solution from step (a) contains from 20 to 40% by wt. of the mixed salts, the amount of said organic solvent added to said aqueous solution in step (b) ranges from 60 to 250% by wt.

4. The method of claim 2, wherein, when the aqueous solution from step (a) contains from 5 to to 15% by wt. of the mixed salts, the amount of said organic solvent added to said aqueous solution in step (b) ranges from 200 to 400% by wt.

5. The method of claim 2, wherein the proportion of salts in the aqueous solution from step (a) ranges from 60 to 80% for potassium arabonate and from 40 to 20% for potassium ribonate.

* * * * *